(12) United States Patent
Williams et al.

(10) Patent No.: US 8,452,380 B2
(45) Date of Patent: May 28, 2013

(54) INTERFACE DEVICE AND PROTOCOL

(75) Inventors: Robert Williams, Fort Salonga, NY (US); Alan Cross-Hansen, Massapequa Park, NY (US); Tito Tengco, Dix Hills, NY (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1539 days.

(21) Appl. No.: 11/568,033

(22) PCT Filed: Apr. 21, 2005

(86) PCT No.: PCT/US2005/013613
§ 371 (c)(1),
(2), (4) Date: Oct. 18, 2006

(87) PCT Pub. No.: WO2005/104697
PCT Pub. Date: Nov. 10, 2005

(65) Prior Publication Data
US 2009/0214094 A1    Aug. 27, 2009

Related U.S. Application Data

(60) Provisional application No. 60/564,674, filed on Apr. 22, 2004.

(51) Int. Cl.
*A61M 5/00*    (2006.01)
(52) U.S. Cl.
USPC ............................ 600/432; 600/431; 600/420
(58) Field of Classification Search
USPC ................ 600/431, 432; 604/131, 19, 30, 67, 604/151, 154, 181, 189, 218; 700/230
See application file for complete search history.

(56) References Cited

U.S. PATENT DOCUMENTS

| | | | |
|---|---|---|---|
| 4,160,308 A | 7/1979 | Courtney et al. | |
| 4,903,705 A | 2/1990 | Imamura et al. | |
| 5,301,672 A | 4/1994 | Kalender | |
| 5,615,091 A | 3/1997 | Palatnik | |
| 6,397,098 B1 * | 5/2002 | Uber et al. | 600/431 |
| 6,638,223 B2 | 10/2003 | Lifshitz et al. | |
| 6,643,537 B1 | 11/2003 | Zatezalo et al. | |
| 6,673,033 B1 | 1/2004 | Sciulli et al. | |
| 6,686,769 B1 | 2/2004 | Nguyen et al. | |

(Continued)

OTHER PUBLICATIONS

European Application No. EP 05739018, Supplemental European Search Report dated Aug. 10, 2011, 2 pages.

*Primary Examiner* — Brian Casler
*Assistant Examiner* — Nasir S Shahrestani
(74) *Attorney, Agent, or Firm* — Fredrikson & Byron, PA

(57) ABSTRACT

The invention is an interface device and system for establishing an operating interface between an injector device and diagnostic imaging equipment. In one embodiment, the interface device may permit an operator to concurrently operate and control the injector device and the imaging equipment. The interface device may permit the injector system and the imaging system to communicate information regarding their current and future operational status with each other. The interface device may be used to synchronize the operation of the imaging equipment and the injector device. In one embodiment, the injector device and the imaging equipment may be able to communicate with each other directly or through the interface device via a communications protocol comprising binary logic signals. The binary logic signals may comprise one or more of a low strength signal, a high strength signal, an oscillating signal that oscillates between low and high signal strength, and combinations thereof.

22 Claims, 9 Drawing Sheets

U.S. PATENT DOCUMENTS

| | | |
|---|---|---|
| 6,714,667 B1 | 3/2004 | Mooney et al. |
| 6,721,391 B2 | 4/2004 | McClelland et al. |
| 7,662,124 B2 * | 2/2010 | Duchon et al. .................. 604/19 |
| 2002/0165445 A1 | 11/2002 | Uber |
| 2002/0183616 A1 | 12/2002 | Toews et al. |
| 2003/0069498 A1 | 4/2003 | Kohls |
| 2003/0195491 A1 | 10/2003 | Schneider et al. |
| 2003/0195651 A1 | 10/2003 | Cherfane et al. |
| 2003/0211188 A1 | 11/2003 | Kachnic |
| 2003/0216643 A1 | 11/2003 | Zatezalo et al. |
| 2004/0024361 A1 | 2/2004 | Fago et al. |
| 2004/0059219 A1 | 3/2004 | Asafusa |
| 2004/0068169 A1 | 4/2004 | Mansfield et al. |
| 2004/0073598 A1 | 4/2004 | Dean et al. |
| 2004/0073603 A1 | 4/2004 | Ellis |
| 2004/0162488 A1 * | 8/2004 | Uber et al. ..................... 600/432 |
| 2004/0254525 A1 * | 12/2004 | Uber et al. ...................... 604/67 |
| 2005/0203389 A1 * | 9/2005 | Williams ...................... 600/431 |
| 2009/0247866 A1 * | 10/2009 | Uber et al. .................... 600/431 |

* cited by examiner

INTERFACE DEVICE AND PROTOCOL

PRIORITY

This application claims priority to PCT Application No. PCT/US2005/013613, filed Apr. 21, 2005 and entitled INTERFACE DEVICE AND PROTOCOL and to U.S. Provisional Application No. 60/564,674, filed Apr. 22, 2004.

BACKGROUND OF THE INVENTION

The invention relates generally to injector and imaging equipment for performing diagnostic imaging on a patient, and more particularly to an interface device for facilitating communication between an injector device and imaging equipment.

In many medical diagnostic procedures, a physician or other person injects a patient with a fluid, such as a contrast media, that is detectable with diagnostic imaging equipment. In recent years, a number of injector-actuated syringes and powered injectors for pressurized injection of fluids have been developed for use in diagnostic imaging procedures such as angiography, computed tomography, ultrasound, and NMR/MRI. In general, the powered injectors and imaging equipment may be monitored and operated with separate interfaces.

The imaging equipment may expose a patient to a determined amount of energy after injection of the fluid. In many circumstances it may be desirable to synchronize the timing of the injection to the exposure of imaging energy. For instance, during a computed tomography (CT) scan, a patient may be initially administered a specified volume of contrast media, (approximately 100 cc) at a desired flow rate (e.g., approximately 3 cc/sec) intravenously using an injector. Depending upon the fluid dynamics of the contrast media being administered to the patient, the particular physiology of the patient, and the anatomical region of the patient being imaged, the patient may be exposed to the imaging equipment's energy for some optimal period of time. The use of separate interfaces for both the injector and the imaging equipment may make synchronization between the devices difficult.

In general, the injection device and the imaging equipment may be located in an imaging room, and the interfaces may be located in a separate imaging control room. The combination of the imaging room and the imaging control room is commonly referred to as an imaging suite. User interface controls for the injector device and the imaging equipment may be primarily, but not always be limited to features associated with patient set-up prior to, or during the early part of exposing the patient to the energy of the imaging equipment. To perform the diagnostic procedure, clinician(s) in the imaging control room may have to program, initiate, monitor, control, and terminate the imaging procedure on two different interfaces. In some cases it may be necessary for the clinician(s) to monitor and control the two interfaces concurrently. There may be situations where the lack of synchronization may result in starting the imaging equipment too early or too late. As a result, image quality may be poor and it may be necessary to repeat the procedure. Restarting the procedure may not desired because it makes the overall process more expensive, less efficient, and the patient may have to be re-exposed to the imagining equipment energy and a re-dosing of injected contrast media.

Thus, there still exists a need for a device and method for concurrently monitoring and controlling an injector device and imaging equipment from a single interface.

BRIEF SUMMARY OF THE INVENTION

In one alternative embodiment, the present invention is directed to an interface device and system for establishing an operating interface between an injector device and diagnostic imaging equipment. In one alternative embodiment, the interface device may permit an operator to concurrently operate and control both the injector device and the imaging equipment. In some embodiments the interface device may permit the injector system and the imaging system to communicate information regarding their current and future operational status with each other. As a result, the interface device may be used to synchronize the operation of the imaging equipment and the injector device.

In one alternative embodiment, the interface device may be adapted for facilitating communication between the injector device and the diagnostic imaging equipment. In one embodiment, the interface device may comprise a control unit having one or more stored imaging equipment operational protocols that may be used to operatively control the operations of the imaging equipment. In one alternative embodiment, the interface device may include a dedicated input that may be in communication with the control unit and may be adapted for receiving information from the imaging equipment, and a dedicated output that may be in communication with the control unit and may be adapted for sending information from the control unit to the imaging equipment. The interface device may also include one or more input/output interfaces that may be in communication with the control unit and may be adapted for sending and receiving information between said control unit and the injector device.

In one alternative embodiment, the stored operational protocols may include operational parameters such as tube current, tube voltage, collimation, pitch, detector configuration, rotation, pause, scan delay, start, and stop. In one alternative embodiment, the interface device may use the operational protocols to synchronize the operation of the imaging device with the injector device. In one embodiment, the interface device may be used to communicate current status of the injector device to the imaging equipment and vice versa. As a result, the imaging equipment and the injector may know the status of each device and may be capable of stopping or starting the injection or the diagnostic imaging at a desired time.

In one alternative embodiment, the injector device and the imaging equipment may be able to communicate with each other directly or through the interface device via a communications protocol comprising binary logic signals. In some embodiments, the binary logic signals may comprise one or more of: a low strength signal, a high strength signal, an oscillating signal that oscillates between low and high signal strength, and combinations thereof. The binary logic signals may be used to communicate various operational states of the injector device and the imaging equipment. In one alternative embodiment, the control unit of the interface device may be configured to convert the binary logic signals into a format that may be recognizable by the control console and/or the injector device.

In one alternative embodiment, the invention may comprise a system for performing diagnostic imaging comprising an injector device adapted for injecting a contrast media into a patient; a piece of diagnostic imaging equipment for producing diagnostic images; an interface device operatively connected to the injector device and the imaging equipment, and capable of communicating information between the injector device and the imaging equipment; and a control console operatively connected to the interface device. In one alternative embodiment, the interface device may comprise a control unit capable of processing information from the imaging equipment and the injector device; one or more stored operational protocols for operating the imaging equipment; and one or more input/output interfaces for communicating information between the injector device and the imaging equipment.

In some embodiments, the interface device may comprise a stand-alone device that may be capable of performing real time analysis of communications between the injector device and the imaging equipment. In one embodiment, the interface may be able to synchronize the functions and operations of the injector device and the imaging equipment in real time. As a result, the need for re-injections or additional scanning procedures may be reduced. Other features of the present invention are set forth in the drawings and detailed description.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 9:
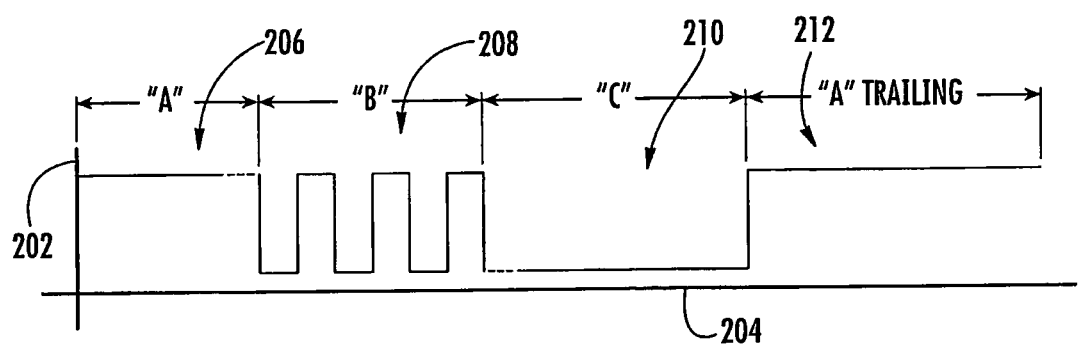
Figure 10:
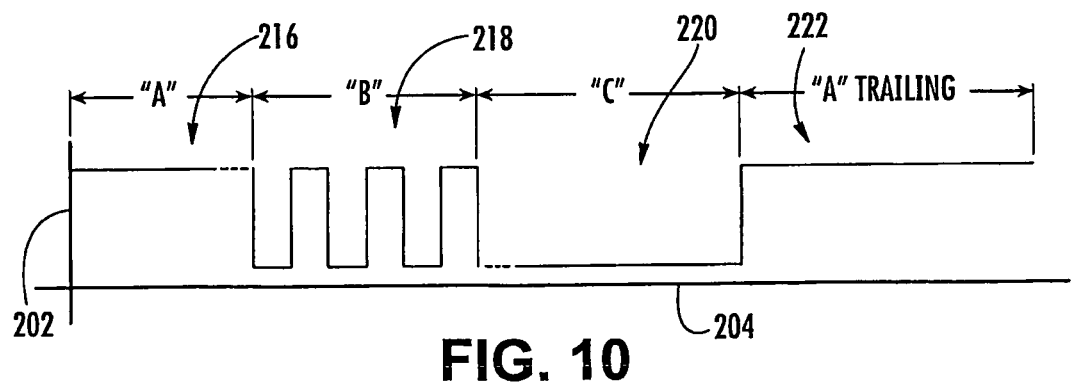

FIG. 9 is a non-limiting description of one alternative embodiment of the present invention showing a graphical representation of a binary logic signal that may be generated by the injector device to communicate information to the imaging equipment; and FIG. 10 is a non-limiting description of one alternative embodiment of the present invention showing a graphical representation of a binary logic signal that may be generated by the imaging equipment to communicate information to the injector device.

DETAILED DESCRIPTION OF THE INVENTION

The present invention now will be described hereinafter with reference to the accompanying drawings. The invention may be embodied in many different forms and the drawings and descriptions herein should not be construed as limited to the embodiments set forth herein. Like numbers refer to like elements throughout.

Figure 1:
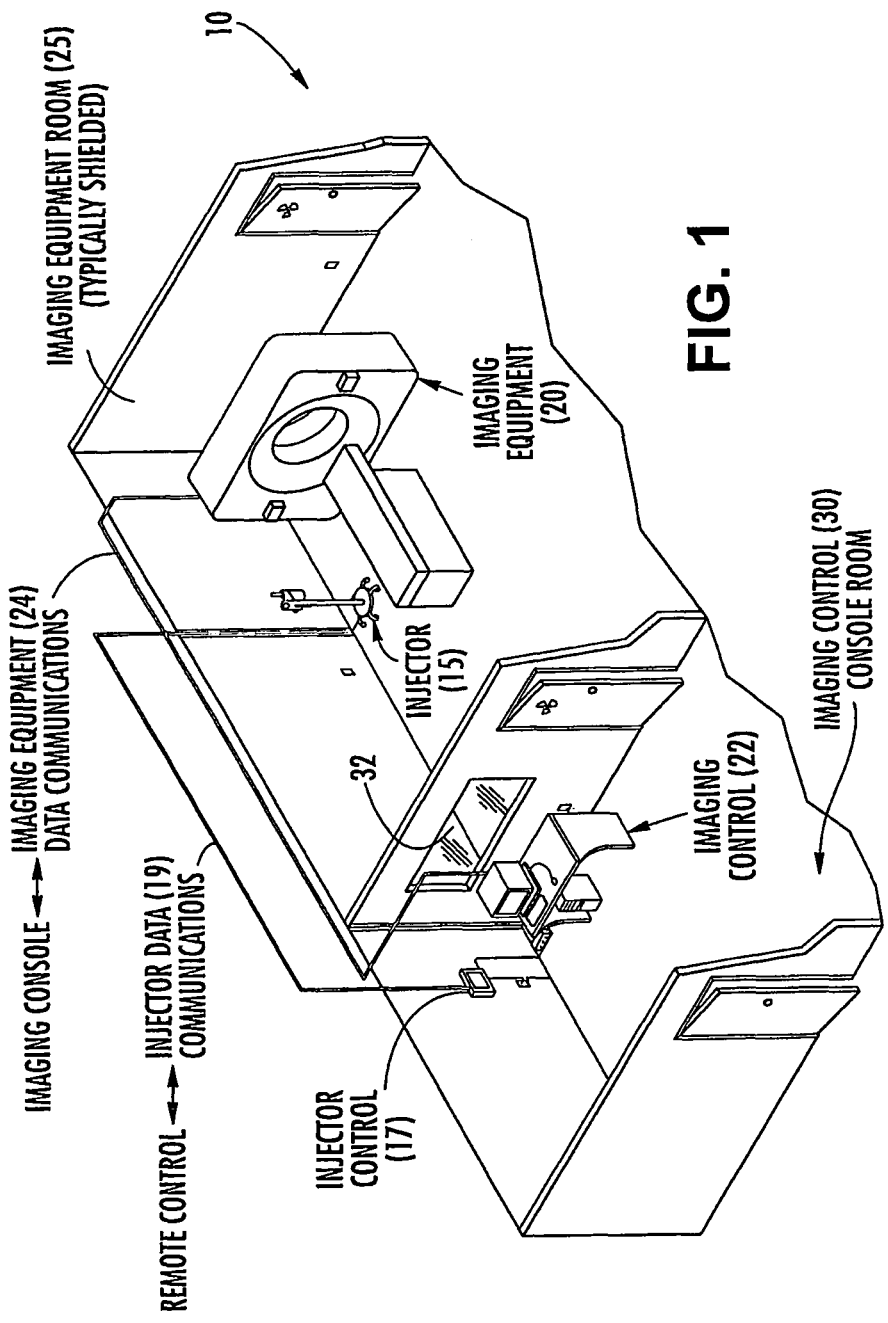
FIG. 1 is a pictorial illustration of a prior art imaging suite having separate remote consoles for the injector device and the imaging equipment.

With reference to the drawings, FIG. 1 generally illustrates a conventional computed tomography (CT) imaging system arrangement located in an imaging suite 10 The CT imaging system typically includes a powered CT injector 15 and CT imaging equipment 20 ("scanner") that are both normally located in an imaging room 25. The CT injector 15 and CT scanner 20 are usually both separately controlled by different remote consoles 17, 22, respectively. The remote consoles 17, 22 may be located externally of the imaging room in a separate control room 30. As shown, the imaging suite may include a viewing window 32 through which the operator may view the procedure. The imaging room 25 may be shielded from electromagnetic interference. Communication lines 19, 24 may separately connect each device to its respective control console. As should be evident from FIG. 1, under the conventional system, the injector and scanner may require separate remote consoles and operation.

In one alternative embodiment, the invention is directed to an imaging system having an interface device for facilitating communication between an injector device and a piece of imaging equipment. The injection/imaging system may comprise an injector system and imaging system that are in communication with and operatively controlled by an interface device.

An injector system may include an injector device that can be used to administer an effective dosage of a contrast medium and a control interface that is operatively connected to the injector device. The injector system may have one or more control interfaces. The control interface may send and receive data to and from the injector device. The injector device can be any type of injector mechanism that may be used to deliver a contrast medium into a patient or subject (e.g., E-Z-EM EMPOWER CT Injector). The imaging system may be comprised of an imaging control console, an imaging device or equipment that can be used to monitor and display the contrast medium within a patient or subject, acquire internal images of a patient or subject, and to provide other diagnostic data to a control console or storage media. The imaging system may have an imaging interface that may be operatively connected to the imaging equipment.

The term "contrast medium" includes any suitable medium, that can be injected into an individual or subject to highlight and/or identify selected areas of the individual's body. Contrast mediums may include, but are not limited to a radio opaque iodinated liquid compound, gadolinium liquid compound, saline media, flush media, and the like, and any combination thereof. A contrast medium may be used in conjunction with an imaging device that is used to perform medical diagnostic imaging such as CT scans, MRI, ultrasound, etc.

Figure 2:
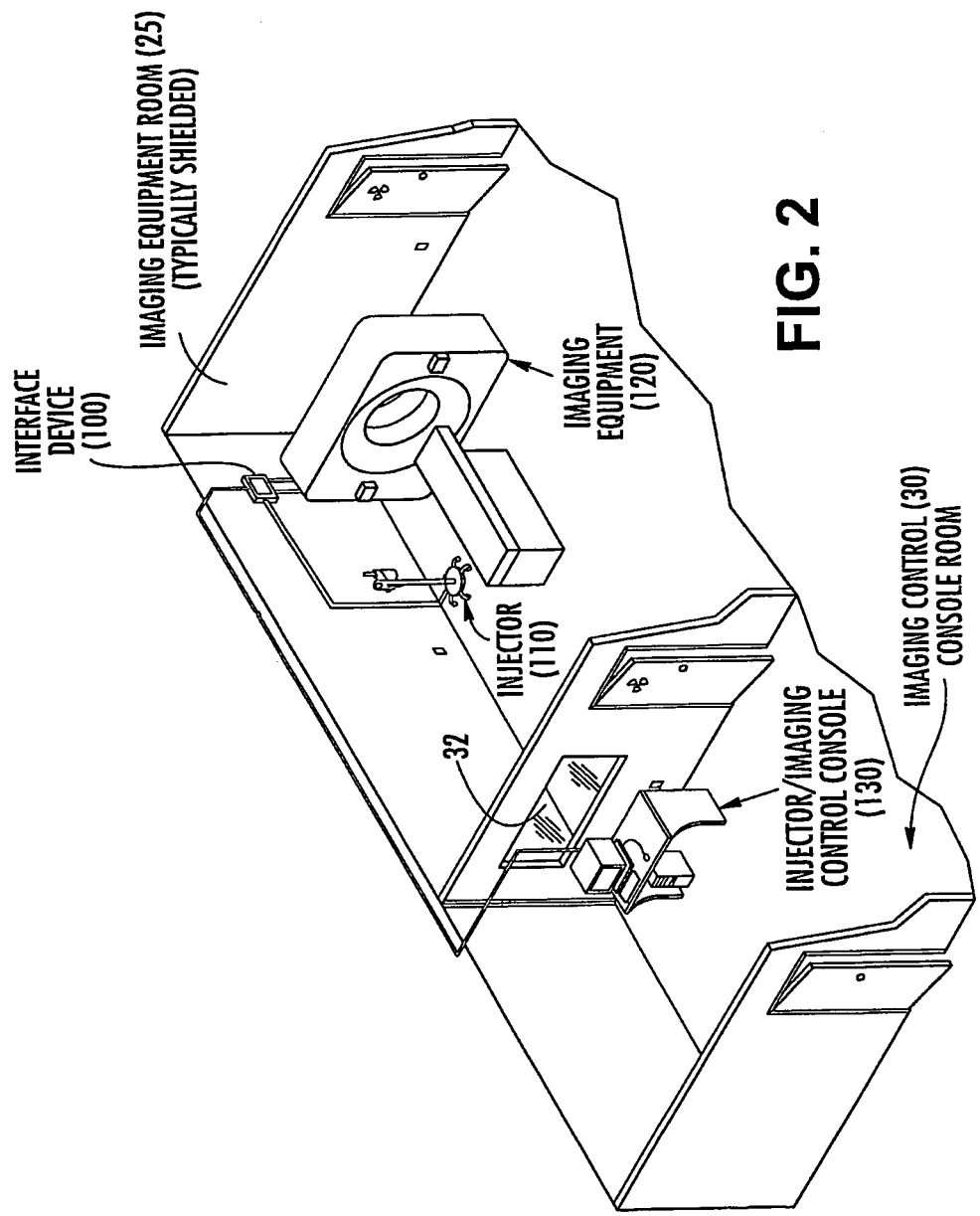
FIG. 2 is a non-limiting description of one alternative embodiment of the present invention showing a pictorial illustration of a diagnostic imaging system having an interface device for facilitating communication between the injector device and the imaging equipment.

In one alternative embodiment, the invention is directed to an interface device that may be used to facilitate communication between an injector device and diagnostic imaging equipment. In this regard, FIG. 2, illustrates an alternative embodiment of the invention depicting an imaging suite wherein a diagnostic imaging system may include an interface device 100 that may help facilitate communication between the injector device 110 and the imaging equipment 120. In one embodiment, the interface device may be a stand-alone device that may function as an intermediate between the injector device and the imaging equipment so that both devices may know the status of the other device in real-time. In some embodiments, the interface devised may be disposed in either the control room or the imaging room. Although the description of the invention primarily discusses the invention with regards to a CT imaging system, it should be recognized that the invention is not limited to CT imaging, and that the invention encompasses a variety of diagnostic imaging procedures which include, but is not limited to, magnetic resonance (MR), ultrasound, angiographic, positron emission topography (PET), fluoroscopy, etc.

In one alternative embodiment, the interface device may comprise a stand-alone device that may permit the injector device to know the current status of the imaging equipment, and the imaging equipment to know the current status of the injector device. In some embodiments, the interface device may be capable of real-time synchronization of the injector device and the imaging equipment. In one alternative embodiment, the interface device may include a microprocessor that may be capable of communicating information received from the imaging equipment or an imaging control console into a format recognizable by the injector device. Such imaging equipment information may include one or more of current status of the imaging device; whether the imaging equipment is in the process of performing a diagnostic scan, whether the imaging scan has halted, and the like. In some embodiments, the microprocessor may be able to receive information from an injector device and convert the information into a format recognizable by the imaging equipment. Such injector information may include one or more of: injector status; whether the injector is armed whereby injector configuration will permit injection; whether the injector is in the process of injecting; whether the injection has stopped or failed to inject, and the like.

A stand-alone interface device having a means of processing information separate from the either the injector console or the imaging console may help improve real-time synchronization between the injector device and the imaging equipment and reduce any latency in processing the information from the injector device and/or imaging equipment. In some embodiments, each manufacturer of diagnostic imaging equipment may develop and determine its own unique communication protocols for communicating with the imaging equipment. Such unique communication protocols may sometimes cause communication delays or latency issues within the control console. The use of a stand alone interface device may help reduce or eliminate such latencies or delays because the interface device may be dedicated to receiving and sending communications between the injector device and the imaging equipment. As a result, the interface device may permit the injector device and the imaging equipment to know the status of the other device in real-time. This information may permit real-time synchronization of the injector device and the imaging equipment.

Figure 3:
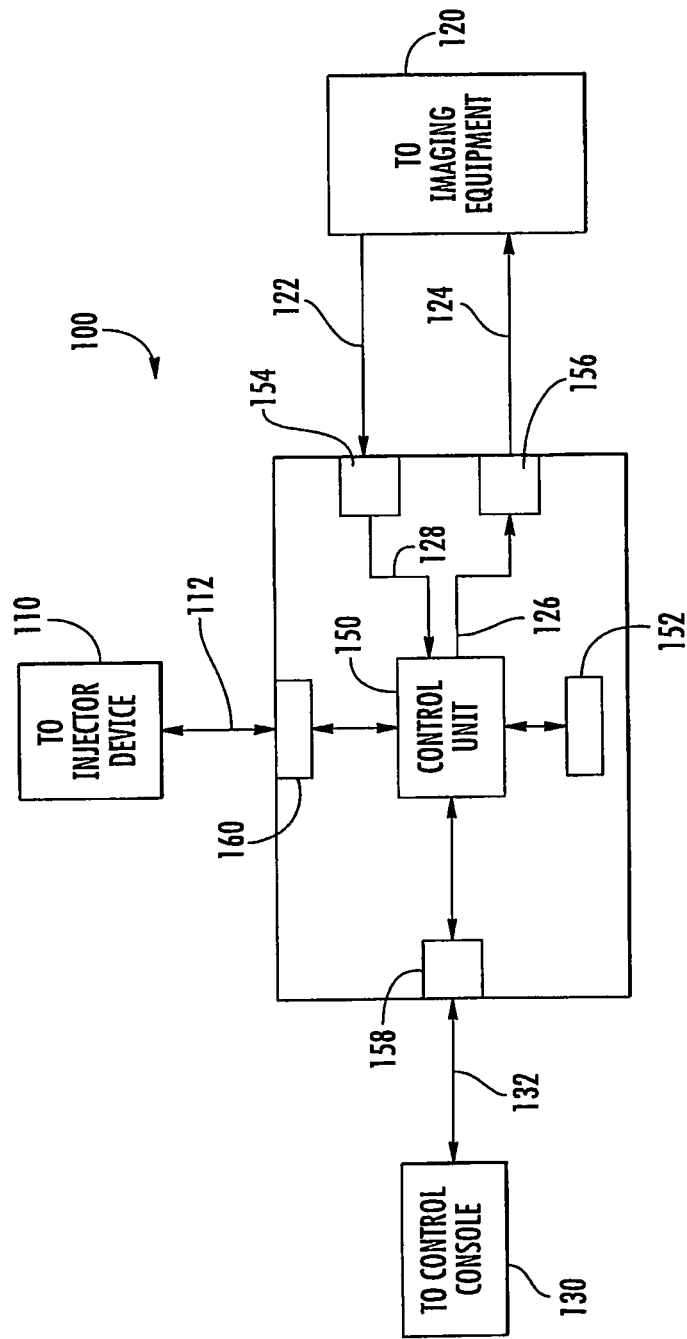
FIG. 3 is a non-limiting description of one alternative embodiment of the present invention showing a schematic illustration of the interface device.

With reference to FIG. 3, an alternative embodiment of the interface device 100 is schematically illustrated. In one alternative embodiment, the interface device 100 may include a control unit 150, a memory component 152, a dedicated input 154 that may be adapted for receiving data from an imaging device or an imaging control console, a dedicated output 156 that may be adapted to communicate injector device status to an imaging device or an imaging control console, one or more (I/O) interfaces 158, 160 that may be adapted for communicating with a remote injector console and/or the injector device. As shown in FIG. 3, the control unit may be operatively connected to the memory component, dedicated input, dedicated output, and the one or more I/O interfaces.

In some embodiments, the dedicated input may be capable of receiving information from the imaging equipment, such as current status, operational state, and the like. In one alternative embodiment, the connection between the dedicated input and the dedicated output on the imaging equipment may comprise a hard wired connection. In some embodiments, the connection 128 between the dedicated input 154 and the control unit 150 may be electrically isolated from the connection 126 between the dedicated output 156 and the control unit 150. For example, such logic level signals carried on 122 and 124 may be managed through a layer of isolation between the connections 154 and 156 and the control unit 150. Although not explicitly shown in the diagram in FIG. 3, opto-isolation components could be used to isolate signals 122 and 124 from one another as well as establishing isolation between the control unit 150 and the imaging equipment 120. The interconnection of the imaging device 100 with the imaging equipment 120 at connection points 154 and 156 may be made with a commercially available type connector. Generic connectors meeting this need may include, for example, commercially available D-subminiature plug socket type connectors and the like.

In one alternate embodiment, the dedicated output may be capable of sending information to the imaging equipment, such as the status of the injector device, whether the injector is stopped, armed, injecting, etc. In some embodiments, the connection between the dedicated output and the control unit may be electrically isolated from the connection between the dedicated input and the control unit.

In some embodiments, the hard wire connection for the dedicated input and output interfaces may include multiple channels that may each be configured to perform different functions. In one alternative embodiment, the dedicated input/output interfaces may comprise a multi-channel connection wherein the connector to the interface device comprises e.g., a 9 to 15 pin socket. The individual pins of each socket may be capable of performing different functions such as, e.g., communicating one or more of: injector status, starting injecting, stop injection, stop diagnostic imaging, start diagnostic imaging, and the like.

In an alternate embodiment, the one or more I/O interfaces 158, 160 may be adapted to send and retrieve information from the injector device and/or the injector remote console. In some embodiments, the I/O interface may comprise wired or wireless connectivity means such as I2C, ACCESS.bus, RS-232, universal serial bus (USB), IEE-488 (GPIB), LAN/Internet protocols such as TCP/IP, wireless means such as infrared (IR) communication, 802.11x, and Bluetooth, etc, and combinations thereof. In some embodiments, the I/O interface may comprise a combination of wired and wireless connectivity means. In one alternative embodiment, the connection between the interface device and the injector device may include a serial connection, such as RS-232.

In some embodiments, the control unit 150 may be in the form of an embedded system comprising a microprocessor or microcontroller configured to perform one or more functions such as converting the imaging equipment communication protocols into a format recognizable by the injector device, or using stored operational protocols to synchronize the injection and imaging processes. As used herein, the term "microcontroller" refers to a microprocessor on a single integrated circuit intended to operate as an embedded system. The microcontroller may also include memory components such as RAM, EEPROM, and PROM, internal timers, and I/O port interfaces. The control unit may include an internal memory component (not shown) that may be an integral part of the control unit. In some embodiments, the control unit may include executable program modules that may be embedded within the internal memory component of the control unit.

In some embodiments, the controller may include a memory component 152 that may be external or internal to the control unit. In one alternative embodiment, the memory component may be configured to buffer information from the imaging equipment and/or the injector device. In some embodiments, the memory component may include flash memory. Flash memory refers generally to a type of nonvolatile memory that can be erased and reprogrammed in units of memory called blocks. The capacity of the memory component can be varied depending upon the desired amount of information that can be stored. In some embodiments the capacity of the memory component may comprise e.g., 64K, 128K, 256K, 512K, 1028 K, 2056 K, or greater memory blocks.

As discussed above, each manufacturer of diagnostic imaging equipment may develop and determine its own unique communication protocols for communicating with the imaging equipment. In some embodiments, the interface device may be programmably configured to store multiple communication protocols in an internal or external memory component. Stored communication protocols may include, but is not limited to one or more protocols for GE, Phillips, Siemens, etc., imaging equipment. The stored communication protocols may permit the interface device to be used with a variety of different imaging equipment. In one alternative embodiment, an operator may be able to select a desired imaging equipment communication protocol from the injector remote console, which may be in communication with the interface device. After an operator selects the appropriate communication protocol, synchronization of the injector and scanner may occur. In addition, in some embodiments the microprocessor may be reprogrammable to include additional communication protocols.

In one alternative embodiment, the manufacturers of the imaging equipment may each develop their own unique operational protocols for operating the imaging equipment. In the context of the invention "operational protocol" includes but is not limited to one or more operating parameters for the imaging equipment or the injector device that may be used to perform specific tests and that can be grouped together and stored for later recall. In some embodiments, the operational protocol may include a grouping of program modules that are used by the control unit of the interface device to instruct the imaging equipment to perform a desired function at a desired time. In the case of a CT scanner, such operating parameters may include, but are not limited to, kV (voltage applied to an X-ray tube, mA (x-ray tube current) detector collimation, pitch (table speed) gantry rotation speed, detector configuration (number of detector slices number and resultant size), automatic control parameters (dose), timed pauses, holds, and/or delays, and the like, and any combination thereof. In some embodiments, the imaging equipment operational parameters may be displayed on a remote control console. In one alternative embodiment, the operating parameters may be manipulated to optimize the imaging and detection data.

In some embodiments, the interface device may be capable of storing multiple operational protocols for multiple manufacturers of imaging equipment. In one alternative embodiment, an operator may select a desired operational protocol for the imaging equipment from a menu screen on the remote console. When a desired operational protocol is selected, the remote console may instruct the interface device to recall the selected operational protocol from its memory component. In some embodiments, the stored operational protocol may then be used by interface device to instruct the imaging equipment to perform one or more operations at a desired time, such as when to begin the diagnostic imaging. For example, in one embodiment, an operator may select an operational protocol for the imaging equipment that specifies that the diagnostic imaging begins at a predetermined time after injection of a contrast media has begun. The interface device, using the selected operational protocol, may monitor the timing of the injection and may instruct the imaging equipment to begin diagnostic imaging at the desired time. As a result, the interface device may help facilitate synchronization of the injector device and the imaging equipment and may help reduce or eliminate the need to have an operator monitoring two consoles to make sure that the sequences of injections and scanning are done at the appropriate time.

Additionally, in some embodiments, the interface device may be used to monitor the status of the injector device and the imaging equipment to ensure that the sequence of operational parameters for the injection device and the imaging equipment are carried out at the appropriate time. For example, the interface device may be used to monitor whether the imaging equipment is in the proper state for performing a diagnostic imaging before the injector device is armed. This may help reduce or eliminate the possibility of injecting a media into a patient prematurely before the imaging equipment is ready to begin diagnostic imaging.

As discussed above, in some alternative embodiments, the interface device may be reprogrammable so that an operator may download additional operational protocols or edit existing protocols in the interface device.

In some embodiments, the interface device may also include stored operational protocols for the injector device. The specific operational parameters may be dependent upon the specific media being injected, the part of the subject being imaged, and the like, and any combination thereof. The media may include contrast media, saline media, and the like, and any combination thereof. Such operational parameters include, but are not limited to, phases, flow rates, volumes, pressures, timed pauses, hold, and delays to x-ray exposure. In one embodiment of the present invention, stored protocols allow operators to quickly recall optimized parameters that can be used in subsequent tests. As a result, the efficiency of the test and imaging quality can be improved.

Alternatively, the operational parameters for the injection device and the imaging equipment may be combined into a single operational protocol. In some embodiments, the combined operational protocol can be displayed on a single display. An operator can use a combined operational protocol to operate the injector device and the imaging equipment. These combined operational protocols may permit an operator to efficiently recall operation parameters for both injector device and the imaging equipment that have been optimized for a specific test. As a result, the efficiency of the test and the image quality can be improved.

In some embodiments, the interface device may be remotely programmable and include separate communications hardware, such as an ISP programming head, for programming the interface device. The interface may also include an I/O buffer for temporarily storing information that can be sent to a manufacturer of the imaging equipment at a desired time.

The interface device may be powered from a variety of different power sources including, but not limited to, a separate AC power supply, a local battery, or from the imaging device or injector device through a wired connection such as a serial connection.

In some embodiments, the interface device may include a means for electrically isolating signals received from the imaging equipment from the injector device, and vice versa. In some cases, medical devices, such as the imaging equipment may be required by the FDA to maintain electrical isolation between electrical circuits and other devices. Electrical isolation may be accomplished in a variety of way including wireless communication between the interface device and either the imaging equipment or injector device, or both. In one alternate embodiment, the interface device may include one or more optically coupled isolators that may be used to establish circuit isolation between the imaging equipment, the injector device, the dedicated input for the imaging equipment, dedicated output for the imaging equipment, or combinations thereof.

Figure 4:
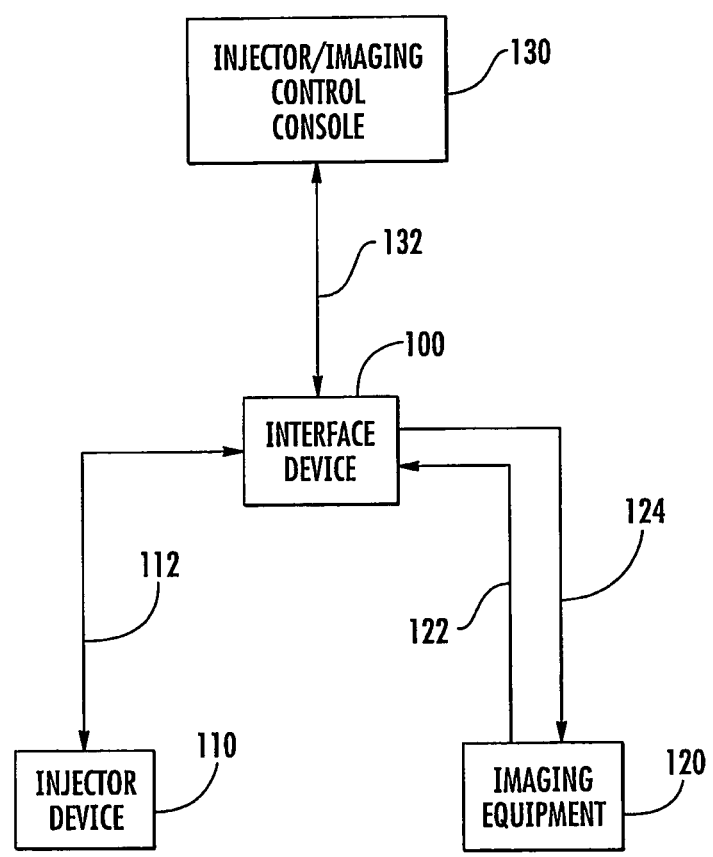
FIG. 4 is a non-limiting description of one alternative embodiment of the present invention showing a block diagram of at least one alternative imaging system having an interface device.

FIGS. 4 through 8, are block diagrams that illustrate alternative embodiments of an imaging system having an interface device that may permit communications between an injector device and the imaging equipment. In FIG. 4 an alternate embodiment of the invention is illustrated wherein the interface device 100 may be disposed between a control console 130 and the injector device 1100 and the imaging equipment 120. The injector device 110 and the control console 130 may be connected to the interface device via connections 112, 132, respectively, which may comprise a wired or wireless connectivity means. In one alternative embodiment, connections 112, 132 may comprise a serial connection, such as RS-232. In one alternative embodiment, the control console 130 may comprise a common control console for operating the imaging equipment and the injector device. In some embodiments, the common control console 130 may be able to instruct the interface device to use a stored operational protocol for operating the imaging equipment in combination with the injector device. The interface device may be operatively connected to the imaging equipment via hard wire connections 122, 124. As discussed above, the input connection from the imaging equipment to the interface device and the output connection to the imaging equipment may comprise a dedicated hard wire connection that may be used to electrically isolate the input and output signals from each other. In one alternative embodiment, the connection between the interface device and the imaging equipment may comprise a wireless connectivity means provided that electrical isolation of the input and output signals may be maintained.

In one alternative embodiment, the common control console 130 may be used to select an operational protocol that may be stored on the interface device 100. The interface device may use the selected operational protocol to synchronize the timing of the diagnostic imaging and the injection. In some embodiments, the interface device may be able to communicate the status of the injector device and/or the imaging equipment to each other in real-time. In some embodiments, the imaging systems may be controlled and operated from a single remote console. As a result, the injection and scanning processes may be synchronized so that the overall process is more efficient and the possibility of having to repeat injections and/or diagnostic imaging may be reduced.

Figure 5:
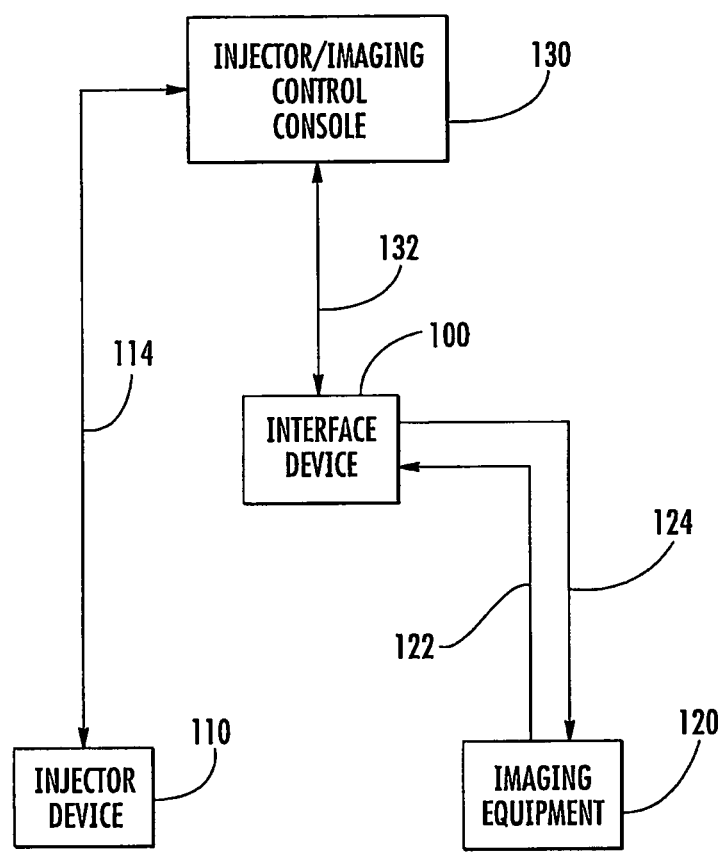
FIG. 5 is a non-limiting description of one alternative embodiment of the present invention showing a block diagram of at least one alternative imaging system having an interface device.

FIG. 5 represents an imaging system wherein the injector device 110 may be connected directly to the control console 130 via connection 114. In this embodiment, the status of the injector device may be relayed to the interface device 100 via the control console. In some embodiments, the interface device may communicate the status of the imaging equipment and instructions through the control console 130. In this embodiment, the interface device may communicate the status of the imaging equipment to the control console 130. The control console 130 may be adapted to instruct the injector device based on the information provided by the interface device. The control console may be adapted to relay injector device information to the interface device, which may be adapted to direct the operation of the imaging equipment based on the information provided by the control console. For example, if the interface device receives information from the control console that indicates that the injector device has started the injection, the interface device may then instruct the imaging equipment to begin the diagnostic imaging at the appropriate time. In some embodiments, if the interface device receives information from the control console that indicates that the injector device has stopped or failed to begin the injection, the interface device may instruct the imaging equipment to stop the diagnostic imaging. In this embodiment, the interface device may also include stored operational protocols that may be used to help synchronize the injecting and imaging processes.

Figure 6:
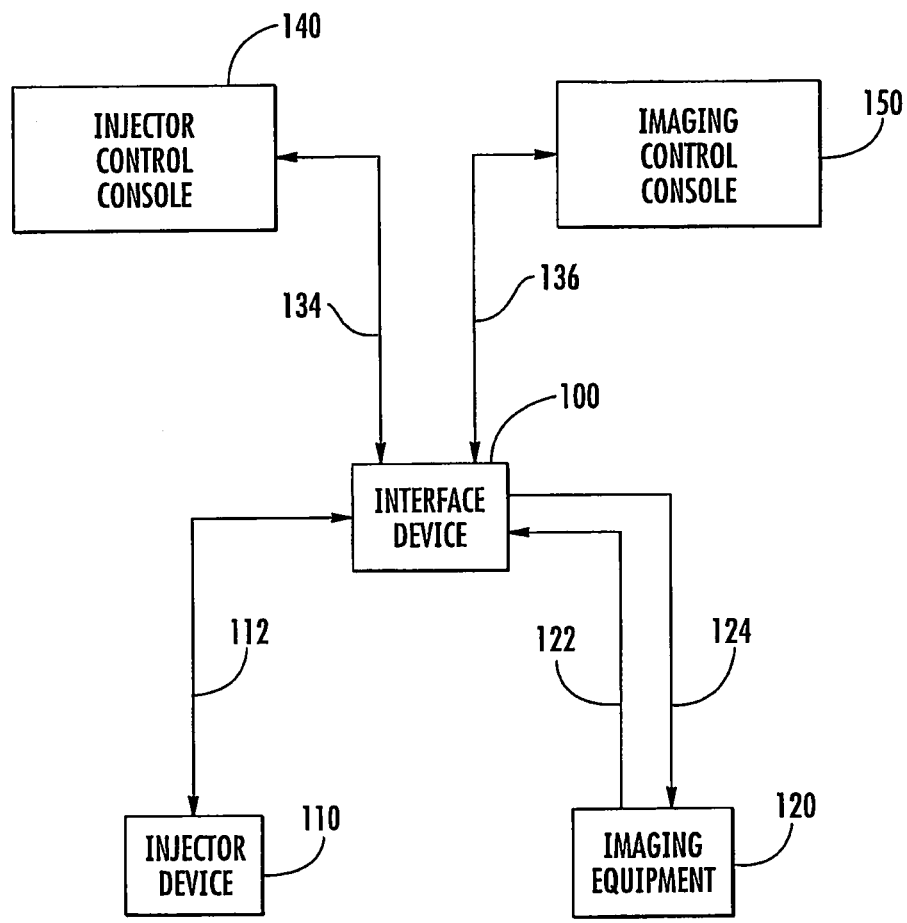
FIG. 6 is a non-limiting description of one alternative embodiment of the present invention showing a block diagram of at least one alternative imaging system having an interface device.

In FIG. 6, the imaging system may include an injector control console 140 and an imaging control console 150 that are both operatively connected to the interface device 100 via connections 134, 136, respectively. In this embodiment, the interface device may use one or more stored operational protocols for controlling the sequence and operations of the injection and the diagnostic imaging. In one alternative embodiment, the interface device may use the operational protocols to directly control the sequence and operations of the injection and imaging processes. As a result, the synchronization of the injector device and the imaging equipment may be improved. In some embodiments, the operation of the injector device and the imaging equipment may be done at either the injector control console or the imaging control console.

Figure 7:
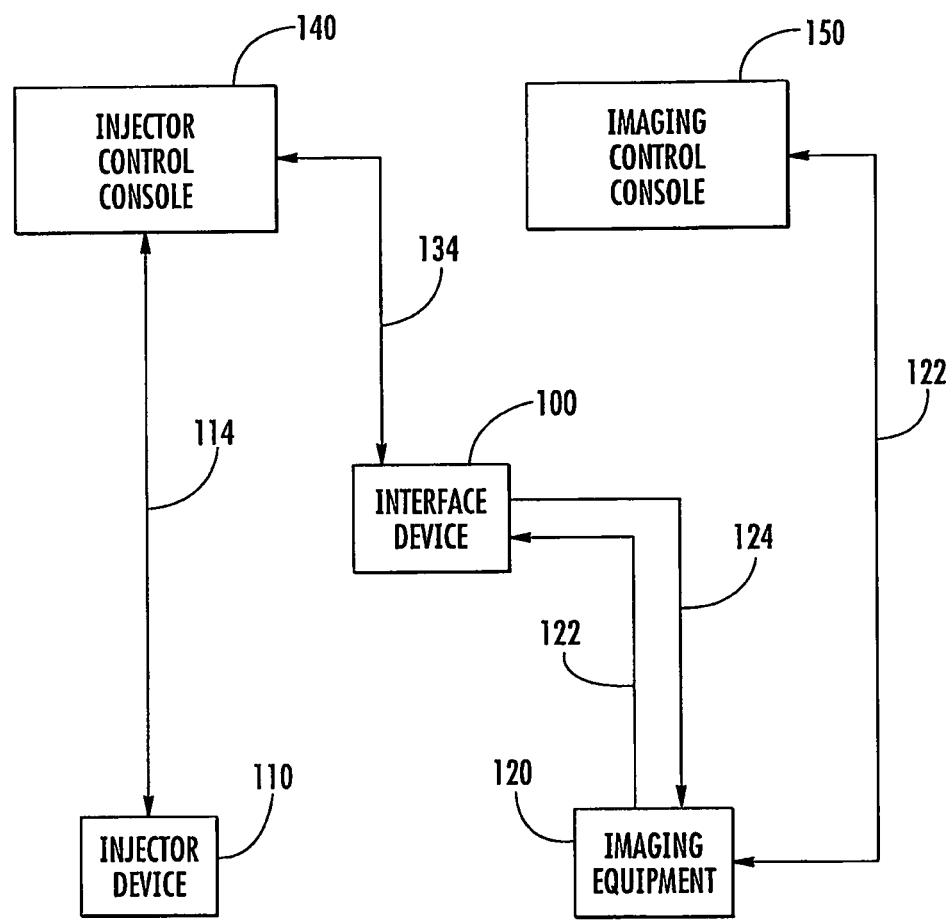
FIG. 7 is a non-limiting description of one alternative embodiment of the present invention showing a block diagram of at least one alternative imaging system having an interface device.

In FIG. 7 an alternate embodiment of the invention is illustrated wherein the injector control console may be directly connected to the injector device via connection 114 and the imaging control console may be directly connected to the imaging equipment via connection 122. In the illustrated embodiment, the injector control console may also be connected to the interface device. In one alternative embodiment, the injector control console 140 may be used to select an operational protocol that may be stored on the interface device 100. The interface device may use the selected operational protocol to synchronize the timing of the diagnostic imaging and the injection.

Figure 8:
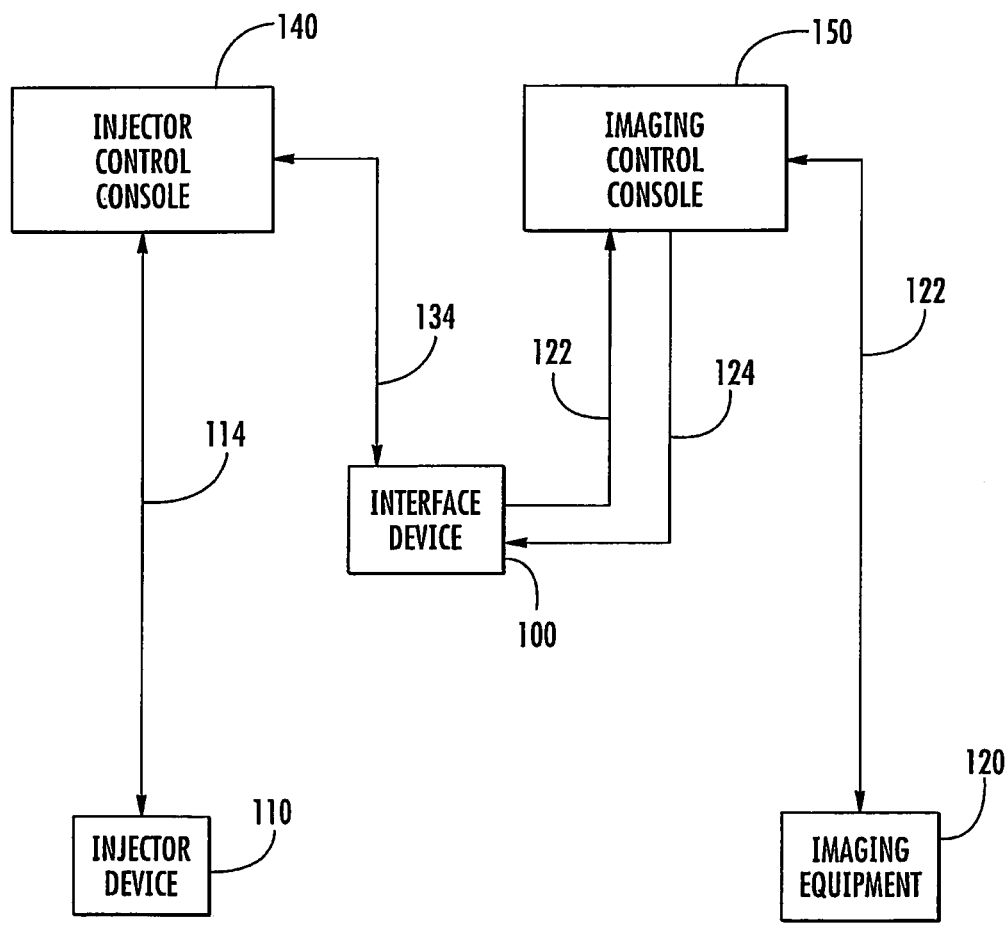
FIG. 8 is a non-limiting description of one alternative embodiment of the present invention showing a block diagram of at least one alternative imaging system having an interface device.

In the alternative embodiment illustrated in FIG. 8, the interface device 100 may function as an intermediate between the injector control console 140 and the imaging control console 150. In this embodiment, the interface device may be used to relay the status of the imaging equipment 120 to the injector control console 140 and the status of the injector device 110 to the imaging control console 150. In this embodiment, the information communicated through the interface device may be used to help synchronize the injection and the diagnostic imaging.

In an alternative embodiment, the imaging equipment may use a communication protocol that comprises logic signals, such as transistor transistor logic (TTL), to communicate information to the injector device. In some embodiments, the logic signals may comprise binary signals having high voltage levels and low voltage levels. In one alternate embodiment, the imaging equipment may use the high and low voltage signals to communicate information to the injector device, and the interface device may use high and low voltage signals to communicate information to the imaging equipment.

Communications in binary logic signals may permit better synchronization between the imaging equipment and the injector device. In particular, the interface device may be able to communicate the state of the injector to the scanner such as, for example, whether the injector is stopped, armed, running, etc. In some embodiments, the interface device may also be able to relay requests for information from the imaging equipment to the injector device, and vice versa. As a result, in some embodiments the imaging device may be capable of knowing such information as when the injector is armed, and may have better control over injector functions. In some prior art methods, it may not have been possible to fully know when it was acceptable for the scanner to start the injection. In one alternative embodiment, the interface device may permit the imaging equipment to know the status of the injector device and may permit the imaging equipment to synchronize the initiation of the diagnostic imaging at a desired time. As a result, the use of the injector device and the imaging equipment may be synchronized so that the injection occurs when the imaging equipment is ready, and the imaging equipment may begin diagnostic imaging at an appropriate moment during the injection cycle.

In some embodiments, the injector device and the imaging equipment may communicate with each other utilizing binary logic signals that may comprise a waveform. In this regard, FIGS. 9 and 10 depict three different binary logic signals that may be used to communicate information between the injector device and the imaging equipment. In some embodiments, the high and low signals may comprise waveforms that are recognizable by the interface device and may be used to communicate information between the imaging equipment and the injector device.

In one alternate embodiment, the injector device may generate one or more voltage signals that may comprise a waveform that is recognizable by the interface device. In this regard, FIG. 9 illustrates several alternate waveforms that may be used to correspond to possible operational states for the injector. FIG. 9 illustrates the strength of the signal 202 plotted against the duration of the signal 204. In one embodiment, the area generated by the high strength signal 206 may corresponds to an operational state of the injector device, such as if the injector device may be in "Stop mode", "awaiting programming and syringe loading," "injector arming," or "injector running" or combinations thereof. Area 210 may represent a low strength signal. In some embodiments, a low strength signal may be used to communicate that the injector device is in the process of injecting. Area 208 may be produced by a voltage signal that may be oscillating between high and low signal strength. Depending upon design and need, the period of the oscillations may be lengthened or shortened to correspond to even more states of the injector. As a result, the interface device may be used to communicate multiple states of the injector device to the imaging equipment. Area 212 may comprise a trailing high strength signal that may be used to communicate that the injector has stopped for any reason. Possible reasons for the injector stoppage include, for example: procedure is complete; an over pressure problem is detected in the syringe; extravastion (injection fluid being detected outside the blood vessel); operator halted injection via panel control; the imaging equipment requesting the injector device to halt the injection, and the like, and combinations thereof.

In one alternative embodiment, the imaging equipment may use a communications protocol comprising a binary logic signal to communicate the status of the imaging equipment to the injector device. With reference to FIG. 10, three exemplary waveforms that correspond to possible operational states of the imaging equipment are illustrated. Similar to signal strengths described above for the injector device, the signal strengths generated by the imaging equipment may also correspond to various states of the imaging equipment. In one alternative embodiment, the area 216 may comprise a high strength signal that may correspond to a communication from the imaging equipment requesting the injector device to go into a "Stop mode," "Pause mode," or to stay in a stop or pause mode. Area 218 may be produced by a signal that is oscillating between high and low signal strength. The period of the oscillations in some embodiments may depend upon the abilities of both the injector device and the imaging equipment. Additionally, depending upon design and need, the period of the oscillations may be lengthened or shortened to correspond to even more operational commands that may be sent from the imaging equipment to the injector device. In on alternative embodiment, area 220 may be produced by a low signal strength that may correspond to a request from the imaging equipment that the injector device go to "Run mode" (start injecting). Area 222 may comprise a trailing high strength signal that may correspond to a request from the scanner that the injector go to "Stop mode". Possible reasons for requesting that the injector device to go to Stop mode may include, for example; the diagnostic imaging has been completed and the imaging equipment may have made a determination not to continue contrast injection; the imaging equipment has experienced a problem and decides not to continue contrast injection; and an emergency stop has been activated for the imaging device and the imaging device decides not to continue the contrast injection.

In one embodiment, the interface device may include one or more program modules that may instruct the interface device to periodically sample the signal strength generated by either the injector device and/or the imaging equipment. In some embodiments, the interface may be configured to sample the signal strength at predetermined time intervals. In one alternate embodiment, the interface device may sample the signal strength to check status of the imaging equipment and the injector device. In one embodiment, the interface device may sample the signal strength to verify that the communication channels with the injector device and/or imaging equipment remains active.

In one alternative embodiment, the binary logic signals may comprise a communication protocol that may be used to facilitate communications directly between the injector device and the imaging equipment. In this embodiment, the binary logic signal may be used as described above without the need to have an intermediary interface device.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Further, throughout the description, where compositions are described as having, including, or comprising specific components, or where processes or methods are described as having, including, or comprising specific steps, it is contemplated that compositions of the present invention may also That which is claimed:

1. An interface device adapted for facilitating communication between an injector device and medical diagnostic imaging equipment, the interface device comprising:
a control unit having one or more stored medical imaging equipment operational protocols for multiple manufacturers of medical imaging equipment, the control unit having one or more stored injector device operational protocols for the injector device for multiple manufacturers of injector devices, the control unit configured to process information from the injector device and the imaging equipment;
a dedicated input in communication with the control unit and configured to receive information from the imaging equipment;
a dedicated output in communication with the control unit and configured to send information from the control unit to the imaging equipment; and
one or more input/output interfaces in communication with the control unit and configured to send and receive information between the control unit and the injector device, the one or more input/output interfaces permitting the selection of a desired medical imaging equipment operational protocol, the one or more input/output interfaces permitting the selection of a desired injector device operational protocol.

2. The interface device according to claim 1, wherein the stored operational protocols include operational parameters for operating the medical imaging equipment.

3. The interface device according to claim 2, wherein the operational parameters include operational parameters selected from the group consisting of tube current, tube voltage, collimation, pitch, detector configuration, rotation, pause, scan delay, start, and stop.

4. The interface device according to claim 1, wherein the stored operational protocols include operational parameters for operating the injector device.

5. The interface device according to claim 1, wherein the interface device is configured to receive and send binary logic signals to and from the medical imaging equipment.

6. The interface device according to claim 5, wherein the binary logic signals comprise transistor transistor logic.

7. The interface device according to claim 1, wherein the interface device is configured to receive and send binary logic signals to and from the injector device, and wherein the binary logic signals comprise transistor transistor logic.

8. The interface device according to claim 1, wherein the control unit comprises a microprocessor.

9. The interface device according to claim 1, wherein the dedicated input and dedicated output are electrically isolated from each other.

10. The interface device according to claim 1, wherein the interface device is reprogrammable.

11. The interface device according to claim 1, wherein the interface device is configured to communicate the operational status of the injector device with the medical imaging equipment, and communicate the operational status of the medical imaging equipment with the injector device.

12. A system for performing diagnostic imaging comprising:
an injector device adapted for injecting a contrast media into a patient;
a piece of medical diagnostic imaging equipment for producing diagnostic images;
an interface device operatively connected to the injector device and the medical imaging equipment, and configured to communicate information between the injector device and the medical imaging equipment, the interface device comprising a control unit capable of processing information from the medical imaging equipment and the injector device;
one or more stored medical imaging equipment operational protocols for multiple manufacturers of imaging equipment, the one or more stored medical imaging equipment operational protocols for operating the medical imaging equipment;
one or more stored injector device operational protocols for multiple manufacturers of injector devices, the one or more stored injector device operational protocols for operating the injector device;
one or more input/output interfaces configured to communicate information between the injector device and the medical imaging equipment, the one or more input/output interfaces permitting the selection of a desired medical imaging equipment operational protocol, the one or more input/output interfaces permitting the selection of a desired injector device operational protocol; and
a control console operatively connected to the interface device.

13. A system according to claim 12, wherein the injector device and the imaging equipment communicate with the interface device via binary logic signals.

14. A system according to claim 13, wherein the binary logic signals include one or more of a low strength signal, a high strength signal, an oscillating signal that oscillate between low and high strength, and combinations thereof.

15. A system according to claim 14, wherein a high strength signal generated by the imaging device comprises a request from the medical imaging equipment that the injector device stops injecting a contrast media into a patient.

16. A system according to claim 14, wherein a low strength signal generated by the imaging device comprises a request from the medical imaging equipment that the injector device starts injecting a contrast media into a patient.

17. A system according to claim 12, wherein the stored operational protocols include operational parameters for operating the medical imaging equipment, and wherein the operational parameters include operational parameters selected from the group consisting of tube current, tube voltage, collimation, pitch, detector configuration, rotation, pause, scan delay, start, and stop.

18. A system according to claim 12, wherein the control unit is configured to synchronize the medical imaging equipment to start diagnostic imaging of the patient at a predetermined time following the injection of a contrast media into the patient.

19. A system according to claim 12, wherein the control unit is configured to instruct the medical imaging equipment to stop diagnostic imaging of the patient based on information received from the injector device.

20. A system according to claim 12, wherein the control unit is configured to instruct the injector device to start injecting a contrast media into the patient based on information received from the imaging equipment.

21. The interface device according to claim 1, wherein the control unit is configured to convert the selected imaging equipment operational protocol into a format recognizable by the injector device.

22. A system according to claim 12, wherein the control unit is configured to convert the selected medical imaging equipment operational protocol into a format recognizable by the injector device.

* * * * *